Dec. 25, 1962 R. O. RUBEL, JR Plant Pat. 2,207
CAMELLIA PLANT
Filed June 15, 1961
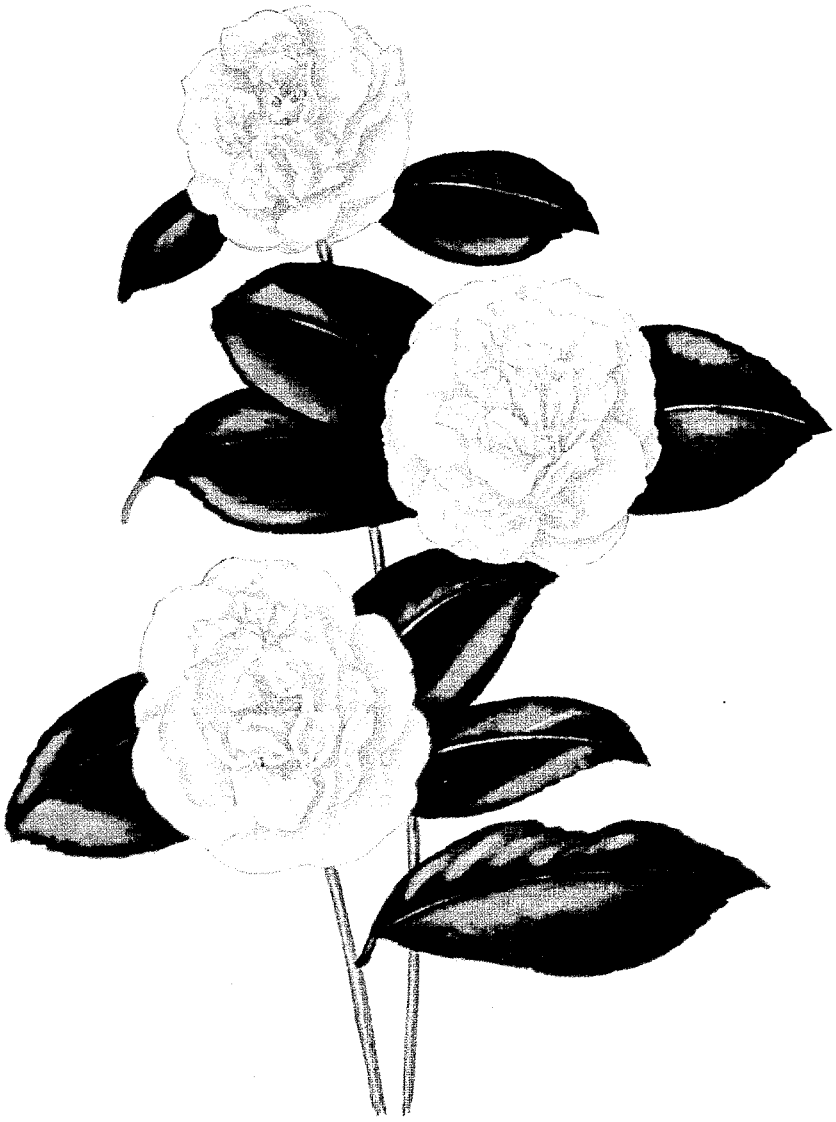
INVENTOR:
ROBERT O. RUBEL, JR.
BY: Rummler & Snow
ATT'YS United States Patent Office Plant Pat. 2,207
Patented Dec. 25, 1962

2,207
CAMELLIA PLANT

Robert O. Rubel, Jr., Crichton Station, Ala., assignor to Cliff Harris, Mobile, Ala.

Filed June 15, 1961, Ser. No. 117,479
1 Claim. (Cl. 47—60)

My present invention concerns a new and distinct variety of camellia plant which was discovered by me in 1939 in the course of my work on nursery grounds at Mobile, Alabama. This new variety occurred as a seedling of unknown parentage and was distinguished by its unusually small, white blooms which are of a double peony form with the inside petals reflecting a delicate yellow glow from the stamens. I further observed that the plant of this unknown seedling, while very similar to other camellias, in size and growth characteristics, produced abundant foliage and bloomed profusely and continuously throughout the fall and winter seasons, with perfect blooms, having excellent keeping qualities, in spite of being subjected to numerous freezes with temperatures as low as 17° F.

Having noted that this new variety was winter hardy and that blooming continued freely after each freeze, I proceeded to propagate the plant asexually, both by rooted cuttings and grafting, at the aforesaid nursery grounds in Mobile, Alabama, and as a result of continued propagation through many generations I have found this new variety to be a true miniature white camellia, with the smallest flower of this form yet known, and that the succeeding generations of the new variety retain all of the characteristics of the original discovery.

The accompanying illustration shows, in full color, typical full-blown blossoms and the foliage of my new variety of camellia plant.

The following is a detailed description of the new variety:

*The Plant*

Origin: Seedling, percentage unknown.
Classification: *Camellia japonica.*
Present method of propagation: Rooted cuttings and grafting.
Form: Compact bush.
Height: Average of camellia plants—varying with age.
Growth: Vigorous, upright and branching.
Leaves:
- *Quantity.*—Abundant.
- *Size of leaf.*—Average—4" long x 2⅞" wide.
- *Shape.*—Ovate, with serrated edges.
- *Texture.*—Leathery, smooth and glossy.
- *Color.*—Upper side—dark green. Under side—light green.
- *Petioles.*—Length ⅜ inch.

*Bud*

Size: ¾ to ⅞ inch long—½ inch diameter.
Form: Elliptic—ovoid. Opens slowly.
Color: Medium green, when sepals first divide. Brownish green, when petals begin to unfurl.
Sepals: 9 in number, upstanding and partially hooded over bud.
Calyx: Broad, of smooth aspect, and does not split.

*Flower*

Blooming habit: Recurrent, blooming profusely, from August through March.
Size: Very small. Diameter, 1½ to 2½ inches; depth, 1½ inches.
Borne: Singly.
Shape: High center.
Petalage:
- *Number.*—Approximately 81 with few petaloids.
- *Arrangement.*—Imbricated, double peony form, with 17 large outer petals arranged in two rows, which support 55 smaller petals closer to the center, and with one row of 9 upstanding large petals encircling stamens at center.
- *Shape.*—Large petals, orbicular. Small petals, spatulate.
- *Color.*—Over-all white, with yellow reflected glow at center from stamens. Outer petal: White, tip to base. Inside petal: White, with yellow glow at base. Reverse sides: White. Petaloids: White.

Persistence: Petals stay on stem with excellent lasting quality, both on plant and as cut flower.
Texture: Soft.
Appearance: Satiny.
Fragrance: None.

*Genital Organs*

Stamens:
- *Length.*—Approximately one inch.
- *Number.*—Approximately 32.
- *Color.*—White.
- *Pollen color.*—Yellow.

*Fruit*

Shape: Usually ovoid.
Fertile: Yes.
Color at maturity: Green.

Having thus disclosed my camellia plant discovery, I claim:

A new and distinct variety of camellia plant, substantially as shown and described, characterized particularly by its very small white blooms of high center double peony form, its hardiness in cold weather, its strong growth habit, and its ability to continue blooming from fall through winter in spite of repeated freezes.

No references cited.